United States Patent [19]

Alker et al.

[11] Patent Number: 4,548,935
[45] Date of Patent: Oct. 22, 1985

[54] DIHYDROPYRIDINE ANTI-ISCHAEMIC AND ANTI-HYPERTENSIVE AGENTS, COMPOSITIONS AND USE

[75] Inventors: David Alker, Eastry, Nr. Deal; Peter E. Cross, Canterbury; Simon F. Campbell, Deal, all of England

[73] Assignee: Pfizer Inc., New York, N.Y.

[21] Appl. No.: 691,971

[22] Filed: Jan. 16, 1985

[30] Foreign Application Priority Data

Jan. 18, 1984 [GB] United Kingdom ............... 8401288

[51] Int. Cl.[4] ................... A61K 31/44; A61K 31/535; C07D 413/14; C07D 417/12
[52] U.S. Cl. .................................. 514/230; 546/277; 546/278; 514/231; 546/280; 546/281; 514/232; 546/283; 546/284; 514/236; 514/245; 514/252; 514/269; 514/314; 514/318; 514/333; 514/336; 514/338; 514/339; 514/340; 514/341; 514/342; 514/343; 544/122; 544/131; 544/212; 544/333; 544/364; 546/167; 546/177; 546/193; 546/194; 546/256; 546/269; 546/270; 546/271; 546/272; 546/274; 546/276
[58] Field of Search ............... 544/122, 131, 212, 333, 544/364; 546/167, 177, 193, 194, 256, 269, 270, 271, 272, 274, 276, 277, 278, 280, 281, 283, 284; 514/230, 231, 232, 236, 245, 252, 269, 318, 333, 336, 338, 339, 340, 341, 342, 343

[56] References Cited

U.S. PATENT DOCUMENTS 4,430,333 2/1984 Campbell et al. ................. 424/266

FOREIGN PATENT DOCUMENTS 100189 2/1984 European Pat. Off. .

Primary Examiner—Robert W. Ramsuer
Attorney, Agent, or Firm—Charles J. Knuth; Albert E. Frost; James M. McManus

[57] ABSTRACT

Dihydropyridine anti-ischaemic and anti-hypertensive agents of the formula:

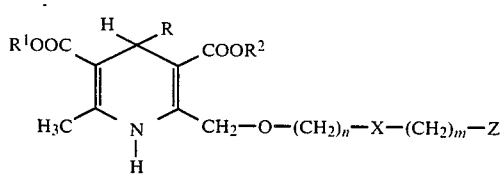

and their pharmaceutically acceptable salts; wherein R is aryl or heteroaryl; $R^1$ and $R^2$ are each independently $C_1$–$C_4$ or 2-methoxyethyl; n is 1 or 2; m is 1, 2 or 3; X is a 5 or 6 membered aromatic heterocyclic group which is linked to the adjacent alkoxymethyl group by a ring carbon atoms thereof; and Z is a group —$NR^3R^4$ or a 5 to 6 membered nitrogen containing heterocyclic group; where $R^3$ is H or $C_1$–$C_4$ alkyl; $R^4$ is H, $C_1$–$C_4$ alkyl, CO($C_1$–$C_4$ alkyl), COCF$_3$, CONR$^5$R$^6$, SO$_2$($C_1$–$C_4$ alkyl) or a heterocyclic or SO$_2$-heterocyclic group, wherein the heterocyclic group is optionally substituted; $R^5$ and $R^6$ and each independently H or $C_1$–$C_4$ alkyl or taken together with the nitrogen atom to which they are attached, they form a pyrrolidinyl, piperidyl, morpholino, piperazinyl or N-($C_1$–$C_4$ alkyl)piperazinyl group.

12 Claims, No Drawings

DIHYDROPYRIDINE ANTI-ISCHAEMIC AND ANTI-HYPERTENSIVE AGENTS, COMPOSITIONS AND USE

BACKGROUND OF THE INVENTION

This invention relates to certain dihydropyridines, specifically to certain 1,4-dihydropyridines having a heterocyclic group in a side chain attached to the 2-position wherein the heterocyclic group is substituted by an aminoalkyl, substituted aminoalkyl or heterocyclylalkyl group, and to pharmaceutical preparations containing such compounds. The compounds have utility as anti-ischaemic and antihypertensive agents.

The compounds of the invention reduce the movement of calcium into the cell and they are thus able to delay or prevent the cardiac contracture which is believed to be caused by an accumulation of intracellular calcium under ischaemic conditions. Excessive calcium influx during ischaemia can have a number of additional adverse effects which would further compromise the ischaemic myocardium. These include less efficient use of oxygen for ATP production, activation of mitochondrial fatty acid oxidation and possibly, promotion of cell necrosis. Thus the compounds are useful in the treatment of prevention of a variety of cardiac conditions, such as angina pectoris, cardiac arrhythmias, heart attacks and cardiac hypertrophy. The compounds also have vasodilator activity since they can inhibit calcium influx in cells of vascular tissue and they are thus also useful as antihypertensive agents and for the treatment of coronary vasospasm.

According to the specification of our European Patent Application No. 60674 there are described and claimed a number of dihydropyridine anti-ischaemic and antihypertensive agents wherein the 2-position of the dihydropyridine ring is substituted with certain mono and disubstituted aminoalkoxymethyl groups. Our European Patent application publication No. 100189 describes and claims a related series of compounds wherein the 2-position is substituted with an aromatic heterocyclalkoxymethyl group. We have now discovered a further series of dihydropyridine compounds having valuable therapeutic properties wherein the heterocyclic group present in the chain at the 2-position bears an aminoalkyl, substituted aminoalkyl or a nitrogen containing heterocyclylalkyl group.

SUMMARY OF THE INVENTION

Thus according to the invention, there are provided novel 1,4-dihydropyridine derivatives of the formula:

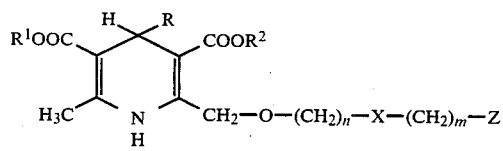

and their pharmaceutically acceptable salts;
wherein
R is aryl or heteroaryl;
$R^1$ and $R^2$ are each independently $C_1$–$C_4$ alkyl or 2-methoxyethyl;
n is 1 or 2;
m is 1, 2 or 3;
X is a 5 or 6 membered aromatic heterocyclic group which is linked to the adjacent alkoxymethyl group by a ring carbon atom thereof; and
Z is a group —$NR^3R^4$ or a 5 or 6 membered nitrogen containing heterocyclic group;
wherein
$R^3$ is H or $C_1$–$C_4$ alkyl;
$R^4$ is H, $C_1$–$C_4$ alkyl, $CO(C_1$–$C_4$ alkyl), $COCF_3$, $CONR^5R^6$, $SO_2(C_1$–$C_4$ alkyl) or a heterocyclic or $SO_2$-heterocyclic group, wherein the heterocyclic group is optionally substituted;
$R^5$ and $R^6$ are each independently H or $C_1$–$C_4$ alkyl or taken together with the nitrogen atom to which they are attached, they form a pyrrolidinyl, piperidyl, morpholino, piperazinyl or N-($C_1$–$C_4$ alkyl)-piperazinyl group.

The term "aryl" as used in this specification for R, includes phenyl and phenyl substituted by one or two substituents each independently selected from nitro, halo, $C_1$–$C_4$ alkyl, $C_1$–$C_4$ alkoxy, hydroxy, trifluoromethyl and cyano. It also includes 1- and 2-naphthyl.

The term "heteroaryl" as used in this specification for R means an aromatic heterocyclic group which may optionally be substituted and includes, for example, benzofuranyl; benzothienyl; pyridyl optionally substituted by methyl, methylthio, cyano or halo; quinolyl; benzoxazolyl; benzthiazolyl; furyl; pyrimidinyl; thiazolyl; 2,1,3-benzoxadiazol-4-yl; 2,1,3-benzthiadiazol-4-yl; and thienyl optionally monosubstituted by halo or $C_1$–$C_4$ alkyl.

The 5 or 6 membered aromatic heterocyclic group X may contain as heteroatom a nitrogen, oxygen or sulphur atom and may also contain up to three further nitrogen atoms. Thus examples of suitable groups for X include tetrazolyl, thiadiazolyl, thiazolyl, thienyl and furyl. The group X is linked to the adjacent alkoxymethyl group by a ring carbon atom, but may be linked to the $(CH_2)_m$—Z group either by a ring carbon or a ring nitrogen atom.

When the group Z is a 5 or 6 membered nitrogen containing heterocyclic group it may be saturated or unsaturated and may contain as heteroatom one or more nitrogen atoms and may also contain an oxygen or sulphur atom. When $(CH_2)_m$—Z is linked to a carbon atom in X, Z may be linked to $(CH_2)_m$ either by a ring carbon or a ring nitrogen atom, but when $(CH_2)_mZ$ is linked to a nitrogen atom in X, Z may only be linked to $(CH_2)_m$ by a ring nitrogen atom when m is 2 or 3. Examples of suitable heterocyclic groups for Z include pyridyl, pyrimidinyl, triazinyl, pyrrolyl, imidazolyl, triazolyl, tetrazolyl, thiazolyl, thiadiazolyl, oxadiazolyl, pyrrolidinyl, piperidyl, morpholino and piperazinyl. The heterocyclic ring may be substituted or unsubstituted. Preferred substituents are $C_1$–$C_4$ alkyl, trifluoroacetyl, arylamino, carbamoyl, methylcarbamoyl, amino or di($C_1$–$C_4$ alkyl)amino groups. Thus particular examples of Z in this aspect include 2-pyridyl, 4-imidazolyl, morpholino, 1,4-piperazinyl, 4-trifluoroacetyl-1-piperazinyl and 4-methylcarbamoyl-1-piperazinyl.

In a further aspect of the invention the group Z is preferably $NH_2$, $NHCH_3$ or $N(CH_3)_2$.

The term "heterocyclic group" when used in connection with $R^4$ means a 5 or 6 membered nitrogen, oxygen, or sulphur containing heterocyclic group which may be saturated or unsaturated and which may optionally include a further one or two nitrogen atoms in the ring and which may optionally be benzofused or substituted with for example, halo, $C_1$–$C_4$ alkyl, hydroxy, acetamido, carbamoyl, methylcarbamoyl, oxo, $NR^8R^9$ or $SO_2NR^8R^9$ groups where $R^8$ and $R^9$ are each independently H, $C_1$-$C_4$ alkyl or phenyl or, taken together with the nitrogen atom to which they are attached, they form a pyrrolidinyl, piperidyl, morpholino, piperazinyl or N-($C_1$-$C_4$ alkyl)piperazinyl group. Particular examples of suitable heterocyclic groups for $R^4$ include pyridyl, pyrimidinyl, quinolyl, thiazolyl and triazolyl.

The term "halo" means fluoro, chloro, bromo or iodo. Alkyl and alkoxy groups having 3 or more carbon atoms can be straight or branched chain. Compounds containing asymmetric centres will exist as one or more pairs of enantiomers and the invention includes the separated d- and l-optically active isomers as well as mixtures thereof.

The pharmaceutically acceptable salts of the compounds of the formula (I) are those formed from acids which form non-toxic acid addition salts, for example the hydrochloride, hydrobromide, sulphate or bisulphate, phosphate or acid phosphate, acetate, citrate, fumarate, gluconate, lactate, maleate, succinate and tartrate salts. In some cases salts may be formed with bases, for example the sodium salt.

Preferred values for R are 2-chlorophenyl and 2,3-dichlorophenyl. $R^1$ and $R^2$ are preferably $CH_3$ or $C_2H_5$; the case where $R^1$ is $CH_3$ and $R^2$ is $C_2H_5$ being especially preferred. Compounds wherein n is 1 and m is 2 are also preferred.

DETAILED DESCRIPTION OF THE INVENTION

The compounds of the invention can be prepared by a number of different processes according to the invention.

(a) In one process the compounds of formula I wherein the group $(CH_2)_mZ$ is linked to a nitrogen atom of the heterocyclic group X may be prepared from a compound of the formula:

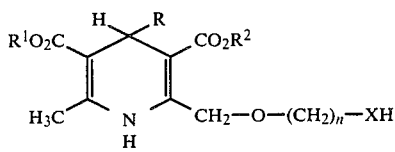

wherein R, $R^1$, $R^2$, n and X are as previously defined, and wherein the heterocyclic group XH contains an NH group as part of the ring, by reacting it with an alkylating agent of the formula:

wherein m and Z are as previously defined and hal is a chlorine or bromine atom.

The reaction is generally performed with the reactants dissolved in a reaction-inert organic solvent (e.g. acetonitrile) in the presence of an acid acceptor (for example potassium carbonate). The reaction can be accelerated by heating and we have found that a period of 24 hours under reflux is generally sufficient to ensure completion of the reaction.

Where the heterocyclic group XH in the compound of formula (II) contains more than one possible position for the NH group, naturally the product is obtained as a mixture of the possible isomers; these can generally be separated by conventional techniques, for example by column chromatography on silica. Thus in the case where the heterocyclic group XH in the compound of formula (II) is a 5-tetrazolyl group, the reaction gives rise to both the 1- and 2-substituted isomers.

Naturally certain of the compounds of formula (I) may be obtained by simple chemical transformation reactions from other compounds of formula (I). Thus, for example, compounds wherein Z is $NR^3R^4$ and $R^3$ and $R^4$ are each hydrogen, may be conveniently prepared by hydrolysis of the corresponding compounds of formula (I) wherein $R^3$ is H and $R^4$ is $COCF_3$ or CO($C_1$-$C_4$ alkyl). The hydrolysis is readily achieved by treating the trifluoroacetyl derivative with dilute aqueous alkali at room temperature for several hours.

The resulting compounds wherein Z is $NH_2$ may be used as the starting material for several of the other compounds of formula (I) in which Z is a substituted amino or heterocyclic group. Thus compounds wherein Z is $NR^3R^4$, $R^3$ is H and $R^4$ is a heterocyclic, $SO_2$($C_1$-$C_4$ alkyl) or a $SO_2$-heterocyclic group may simply be prepared by reaction of the compound of formula (I) wherein Z is $NH_2$ with an appropriate halo-substituted heterocyclic compound or with a $C_1$-$C_4$ or heterocyclyl sulphonyl halide.

In some instances compounds wherein Z is $NR^3R^4$, $R^3$ is H and $R^4$ is a heterocyclic group may also be prepared from the amine where Z is $NH_2$. Thus, for example reaction with dimethyl N-cyanoimidodithiocarbonate gives the 3-cyano-2-methyl-1-isothiourea which may be further reacted with hydrazine hydrate to yield the corresponding compound of formula (I) wherein $R^4$ is a 3-amino-1,2,4-triazol-5-yl group. Alternatively reaction of the amine of formula (I) where Z is $NH_2$ with thiophosgene followed by reaction with ammonia and ethyl bromoacetate yields the compound of formula I wherein $R_4$ is a 4,5-dihydro-4-oxo-2-thiazolyl group.

Again, compounds in which the group Z is a heterocyclic group or wherein Z is $NR^3R^4$ and $R^4$ is a heterocyclic or $SO_2$-heterocyclic group a can undergo further conventional transformation reactions to introduce various substituent groups into the heterocyclic rings. Thus, for example, reaction of a compound wherein Z is a 1-piperazinyl group with methyl isocyanate yields the corresponding compound wherein Z is a 4-(N-methylcarbamoyl)-1-piperazinyl group.

All these transformation reactions are entirely within the knowledge and skill of those skilled in the art and appropriate reagents and conditions for their performance will be well known as will other variations and possibilities.

(b) In an alternative synthesis, compounds in which X is a 1,3,4-thiadiazolyl group are prepared from a compound of the formula:

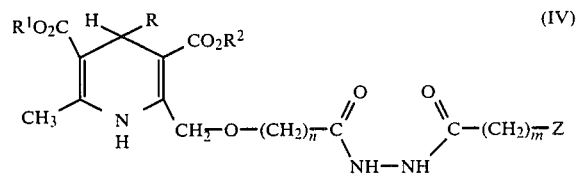

wherein R, $R^1$, $R^2$, n, m and Z are as previously defined. Ring closure is effected by reaction with para-methoxyphenylthionophosphine (Lawesson's reagent) to give the compound of formula (I) wherein the group X is a 5-substituted-1,3,4-thiadiazol-2-yl group.

The reaction is conveniently effected by adding the reagent at room temperature to a solution of the compound (IV) in an inert organic solvent e.g. acetonitrile. After a period of one or two days the solvent is removed and the product isolated and purified as necessary.

The starting compounds of formula (IV) are prepared from the corresponding 2-carboxyalkoxymethyldihydropyridine by reacting with an appropriately substituted hydrazine of formula $Z-(CH_2)_m CONHNH_2$. This is readily achieved at room temperature in an organic solvent using a conventional diimide condensing reagent.

(c) In a further alternative process compounds wherein the group X is a 2,4-thiazolyl group may be prepared by reacting a compound of the formula:

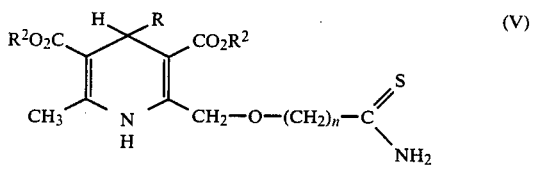

with a compound of the formula:

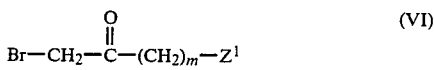

wherein R, $R^1$, $R^2$, n and m are as previously defined and $Z^1$ is as defined for Z and wherein any amino group is optionally protected with a selectively removable amino protecting group. A preferred way of protecting an amino group in this process is as the phthalimido group.

The reaction between the compounds of formula (V) and (VI) is generally achieved by heating the reactants in more or less equimolar proportions in a reaction-inert organic solvent, for example ethanol. A period of 3 to 6 hours is generally sufficient under these conditions and the desired product is then isolated and purified if necessary using conventional techniques. In the case where $Z^1$ is a protected amino group, the final product wherein Z is $NH_2$ is obtained by removal of the protecting group. Thus in the case of compounds where $Z^1$ is a phthalimido group, reaction with, for example, aqueous methylamine may be employed to yield the compound wherein Z is $NH_2$.

(d) In a further process the compounds of formula I can be prepared by the Hantzsch synthesis, according to the following reaction scheme:

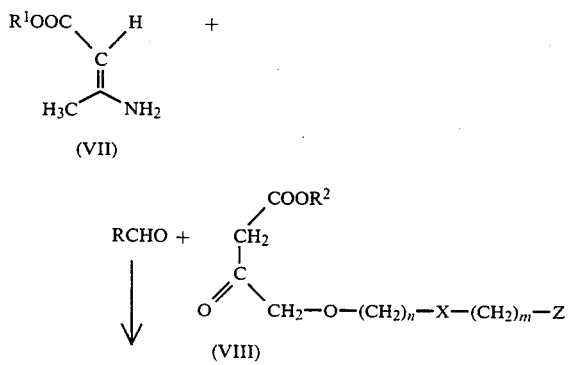

In a typical procedure, the ketoester (VIII) and aldehyde are heated under reflux in a suitable organic solvent, e.g. a $C_1$-$C_4$ alkanol such as ethanol, for about 15 minutes, and then the aminocrotonate (VII) is added. Alternatively the aminocrotonate (VII), the ketoester (VIII) and the aldehyde can be heated together in the solvent. Preferably a small amount of a lower alkanoic acid such as acetic acid is added to neutralise the solution. The resulting solution can then be heated at 60°–130° C., preferably under reflux, until the reaction is essentially complete, typically in 24 hours or less. The product of the formula (I) can then be isolated and purified by conventional procedures, for example by solvent partition, recrystallisation or by chromatography.

The ketoesters (VIII) are either known compounds or can be prepared by methods analogous to those of the prior art. Similarly the amino-crotonates (VII) and the aldehydes are either known compounds or can be prepared by conventional procedures in accordance with literature precedents.

The ability of the compounds to inhibit the movement of calcium into the cell is shown by their effectiveness in reducing the response of isolated heart tissue to an increase in calcium ion concentration in vitro. The test is performed by mounting spirally cut strips of rat aorta with one end fixed and the other attached to a force transducer. The tissue is immersed in a bath of physiological saline solution containing potassium ions at a concentration of 45 millimolar and no calcium. Calcium chloride is added to the bath with a pipette to give a final calcium ion concentration of 2 millimolar. The change in tension caused by the resulting contraction of the tissue is noted. The bath is drained and replaced with fresh saline solution and after 45 minutes, the procedure is repeated with the particular compound under test present in the saline solution. The concentration of compound required to reduce the response by 50% is recorded.

The antihypertensive activity of the compounds is also evaluated after oral administration by measuring the fall in blood pressure in spontaneously hypertensive rats or renally hypertensive dogs.

For administration to man in the curative or prophylactic treatment of cardiac conditions and hypertension, oral dosages of the compounds is generally in the range of from 2–100 mg daily for an average adult patient (70 kg). Thus for a typical adult patient, individual tablets or capsules contain from B 1 to 10 mg of active compound, in a suitable pharmaceutically acceptable vehicle or carrier. Dosages for intravenous administration are typically within the range 1 to 10 mg per single dose as required. In practice the physician will determine the actual dosage which will be most suitable for an individual patient and it will vary with the age, weight and response of the particular patient. The above dosages are exemplary of the average case but there can, of course, be individual instances were higher or lower dosage ranges are merited, and such are within the scope of this invention.

For human use, the compounds of the formula (I) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic.

Thus in a further aspect the invention provides a pharmaceutical composition comprising a compound of the formula (I), or a pharmaceutically acceptable acid addition salt thereof, together with a pharmaceutically acceptable diluent or carrier.

The invention also provides a compound of the formula (I) or a pharmaceutically acceptable acid addition salt thereof, for use in medicine including use in the prevention or treatment of cardiac conditions, or use as an antihypertensive, in man.

The preparation of the compounds of the invention is illustrated by the following Examples.

EXAMPLES 1 AND 2

5-{[4-(2-Chlorophenyl)-3-ethoxycarbonyl-5-methoxycarbonyl-6-methyl-1,4-dihydropyridin-2-yl]methoxymethyl}-2-[2-(N-trifluoroacetylamino)ethyl]tetrazole and 5-{[4-(2-chlorophenyl)-3-ethoxycarbonyl-5-methoxycarbonyl-6-methyl-1,4-dihydropyridin-2-yl]methoxymethyl}-1-[2-(N-trifluoroacetylamino)ethyl]tetrazole A mixture of 5-{[4-(2-chlorophenyl)-3-ethoxycarbonyl-5-methoxycarbonyl-6-methyl-1,4-dihydropyridin-2-yl]methoxymethyl}tetrazole (0.95 g), 1-bromo-2-(N-trifluoroacetylamino)ethane (1.10 g) and potassium carbonate (0.69 g) in acetonitrile (30 ml) was heated under reflux for 24 hours, filtered and evaporated. Thin layer chromatography showed that the resulting oil contained two products. This mixture was separated by chromatography on silica (12 g) using dichloromethane with the addition of from 0 to 50% by volume of ethyl acetate as eluant. Appropriate fractions were combined and evaporated and the residual oils were triturated with diethyl ether. The resulting solids were collected, washed with diethyl ether and dried:

(i) The less polar product was identified as the 2-isomer (0.45 g), m.p. 123°–125° C. Found: C,48.92; H,4.57; N,14.21. $C_{24}H_{26}ClF_3N_6O_6$ requires: C,49.11; H,4.46; N,14.31%.

(ii) The more polar product was identified as the 1-isomer (179 mg), m.p. 155°–156° C. Found: C,49.56; H,4.54; N,14.16. $C_{24}H_{26}ClF_3N_6O_6$ requires: C,49.11; H,4.46; N,14.31%.

EXAMPLES 3–18

The following compounds were prepared by the method described above for Examples 1 and 2 from 5-{[4-(2,3-dichlorophenyl)-3-ethoxycarbonyl-5-methoxycarbonyl-6-methyl-1,4-dihydropyridin-2-yl]methoxymethyl}tetrazole and the appropriate alkylating agent in the presence of potassium carbonate. Both the 1- and 2-isomers were obtained from each reaction and these were separated by chromatography as described above for Examples 1 and 2.

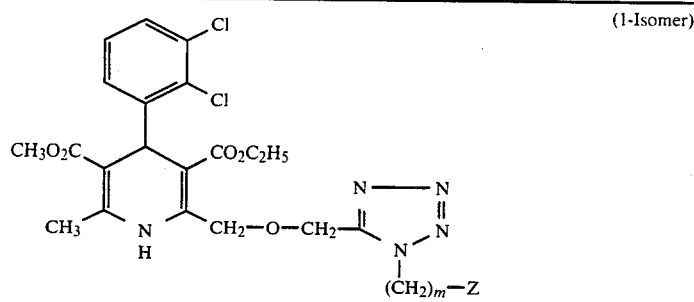
(1-Isomer)
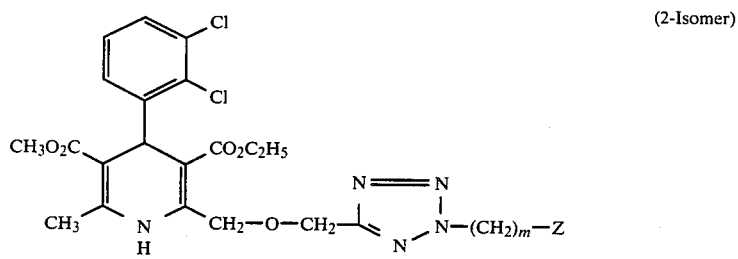
(2-Isomer)
| Example No. | —(CH₂)ₘ—Z | Isomer | m.p. (°C.) | Analysis % (Theoretical in Brackets) | | |
|---|---|---|---|---|---|---|
| | | | | C | H | N |
| 3 | —CH₂CH₂NHCOCF₃ | 2 | 175–177 | 46.51 (46.39 | 4.14 4.06 | 13.69 13.53) |
| 4 | —CH₂CH₂NHCOCF₃ | 1 | 176–178 | 46.57 (46.39 | 4.23 4.06 | 13.41 13.53) |
| 5 | —CH₂CH₂N(CH₃)₂ | 2 | 151–154 | 52.29 (52.08 | 5.62 5.46 | 15.25 15.19) |
| 6 | —CH₂CH₂N(CH₃)₂ | 1 | 157–159 | 52.09 (52.08 | 5.52 5.46 | 15.07 15.19) |
| 7 | —CH₂CH₂N(morpholino) | 2 | 101–103 | 52.35 (52.44 | 5.49 5.42 | 13.86 14.11) |
| 8 | —CH₂CH₂—N(morpholino) | 1 | 192–194 | 52.28 (52.44 | 5.41 5.42 | 13.61 14.11) |
| 9 | —CH₂-(triazine with NH₂, NHC₆H₅) | 2 | 112–114 (dec.) | 53.03 (52.87 | 4.61 4.44 | 19.83 20.55) |
| 10 | —CH₂-(triazine with NH₂, NHC₆H₅) | 1 | 121–125 (dec.) | 53.42 (53.50 | 4.79 4.74 | 19.75 19.82)[1] |
| 11 | —CH₂-(2-pyridyl) | 2 | 145–147 | 54.59 (54.46 | 4.63 4.57 | 14.73 14.66) |
| 12 | —CH₂-(2-pyridyl) | 1 | 114–115 | 54.21 (54.46 | 4.67 4.57 | 15.01 14.66) |
| 13 | —CH₂CH₂CH₂N(CH₃)₂ | 2 | 117–119 | 52.60 | 5.59 | 14.81 |

-continued

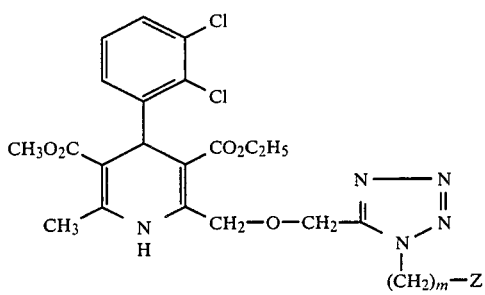
(1-Isomer)

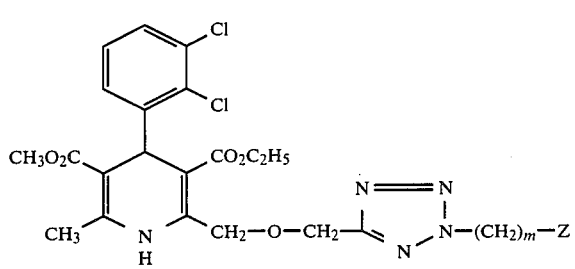
(2-Isomer)

| Example No. | —(CH₂)ₘ—Z | Isomer | m.p. (°C.) | Analysis % (Theoretical in Brackets) C | H | N |
|---|---|---|---|---|---|---|
| 14 | —CH₂CH₂CH₂N(CH₃)₂ | 1 | 176–178 | (52.91 52.65 (52.91 | 5.64 5.69 5.64 | 14.81) 14.76 14.81) |
| 15 |  | 2 | 80 | 50.90 (51.24 | 4.69 4.45 | 16.67 17.44) |
| 16 |  | 1 | 85–90 | 50.88 (51.24 | 4.49 4.45 | 17.69 17.44) |
| 17 | 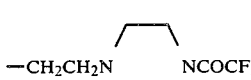 | 2 | 110–111 | 47.47 (47.45 | 4.63 4.80 | 13.88 13.84)[2] |
| 18 | 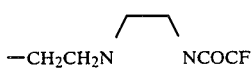 | 1 | 160–162 | 48.47 (48.70 | 4.86 4.63 | 13.92 14.20) |

(1) This product was characterised with 0.25 moles diisopropyl ether of crystallisation.

(2) This product was characterised as a monohydrate.

EXAMPLE 19

2-(2-Aminoethyl)-5-{[4-(2-chlorophenyl)-3-ethoxycarbonyl-5-methoxycarbonyl-6-methyl-1,4-dihydropyridin-2-yl]methoxymethyl}tetrazole 1M Aqueous sodium hydroxide solution (2 ml) was added to a solution of 5-{[4-(2-chlorophenyl)-3-ethoxycarbonyl-5-methoxycarbonyl-6-methyl-1,4-dihydropyridin-2-yl]methoxymethyl}-2-[2-(N-trifluoroacetyl)aminoethyl]tetrazole (0.41 g) in dioxane (15 ml) and the mixture was stirred at room temperature for 3 hours and then evaporated. The residue was partitioned between ethyl acetate and water and the organic layer washed with water, dried over anhydrous sodium sulphate and evaporated. The residual oil was triturated with diethyl ether and the resulting solid collected, washed with diethyl ether and dried to give the title compound (173 mg), m.p. 126°–127° C. Found: C,52.92; H,5.63; N,17.09. $C_{22}H_{27}ClN_6O_5$ requires: C,53.04; H,4.47; N,17.19%.

EXAMPLES 20–24

The following compounds were prepared by the method described above for Example 19 by reacting the appropriate N-trifluoroacetyl compound with 1M aqueous sodium hydroxide solution.

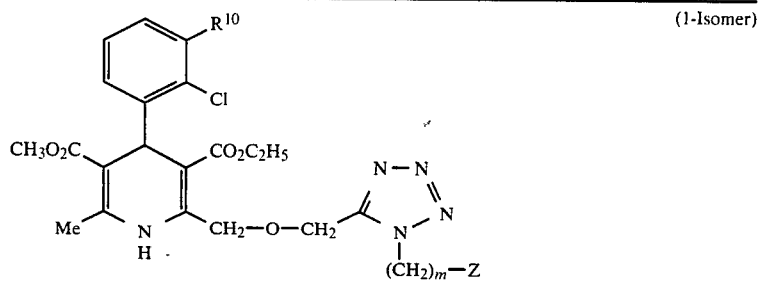
(1-Isomer)

and

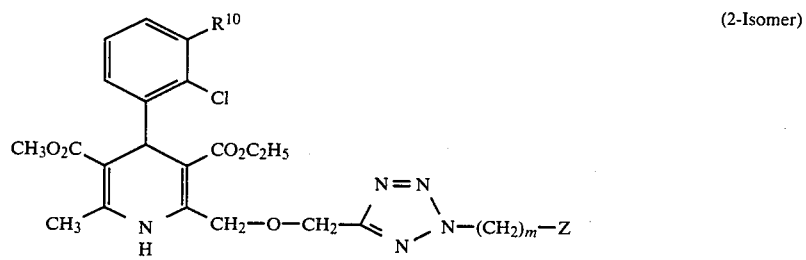
(2-Isomer)

| Example No. | —(CH₂)ₘ—Z | R¹⁰ | Isomer | Form Characterised | m.p. (°C.) | Analysis % (Theoretical in Brackets) C | H | N |
|---|---|---|---|---|---|---|---|---|
| 20 | —CH₂CH₂NH₂ | H | 1 | Free base | — | Hygroscopic, characterised by n.m.r. spectroscopy | | |
| 21 | —CH₂CH₂NH₂ | Cl | 2 | Free base | 109–110 | 49.97 (50.29 | 4.97 4.95 | 16.06 16.00) |
| 22 | —CH₂CH₂NH₂ | Cl | 1 | Free base | 70–75 (dec.) | 49.80 (50.29 | 4.89 4.95 | 15.64 16.00) |
| 23 | —CH₂CH₂N⌒NH | Cl | 2 | Hydrate | 103–105 | 50.80 (50.98 | 5.37 5.71 | 16.09 16.01) |
| 24 | —CH₂CH₂N⌒NH | Cl | 1 | Hemihydrate | 174–176 | 51.79 (51.74 | 5.60 5.64 | 15.90 16.23) |

EXAMPLE 25

5-{[4-(2,3-Dichlorophenyl)-3-ethoxycarbonyl-5-methoxycarbonyl-6-methyl-1,4-dihydropyridin-2-yl]methoxymethyl}-2-{2-[4-(N-methylcarbamoyl)-1-piperazinyl]ethyl}-tetrazole A solution of 5-{[4-(2,3-dichlorophenyl)-3-ethoxycarbonyl-5-methoxycarbonyl-6-methyl-1,4-dihydropyridin-2-yl]methoxymethyl}-2-[2-(1-piperazinyl)ethyl]tetrazole (321 mg) and methyl isocyanate (0.5 ml) in dichloromethane (10 ml) was stirred at room temperature for 30 minutes and evaporated. The residual oil was triturated with diethyl ether and the resulting solid collected, washed with diethyl ether and dried to give the title compound as a hemihydrate (383 mg), m.p. 112°–114° C. Found: C,50.78; H,5.59; N,16.89. $C_{26}H_{33}Cl_2N_7O_5.0.5H_2O$ requires: C,50.91; H,5.60; N,16.96%.

EXAMPLE 26

5-{[4-(2,3-Dichlorophenyl)-3-ethoxycarbonyl-5-methoxycarbonyl-6-methyl-1,4-dihydropyridin-2-yl]methoxymethyl}-1-{2-[4-(N-methylcarbamoyl)-1-piperazinyl]ethyl}-tetrazole This compound was prepared by the method described in Example 25 but starting with 5-{[4-(2,3-dichlorophenyl)-3-ethoxycarbonyl-5-methoxycarbonyl-6-methyl-1,4-dihydropyridin-2-yl]methoxymethyl}-1-[2-(1-piperazinyl)ethyl]tetrazole. The product was characterised as its hemihydrate, m.p. 95°–96° C. Found: C,51.19; H,5.81; N,16.60. $C_{26}H_{33}Cl_2N_7O_5.0.5H_2O$ requires: C,50.91; H,5.60; N,16.96%.

EXAMPLE 27

2-{2-[(3-Amino-1,2,4-triazol-5-yl)amino]ethyl}-5-{[4-(2,3-dichloro-phenyl)-3-ethoxycarbonyl-5-methoxycarbonyl-6-methyl-1,4-dihydropyridin-2-yl]methoxymethyl}tetrazole (A) A solution of 2-(2-aminoethyl)-5-{[4-(2,3-dichlorophenyl)-3-ethoxycarbonyl-5-methoxycarbonyl-6-methyl-1,4-dihydropyridin-2-yl]methoxymethyl} tetrazole (1.04 g) and dimethyl N-cyanoimidodithiocarbonate (0.30 g) in propan-2-ol (10 ml) was heated under reflux for 16 hours and then evaporated. The residual oil was triturated with hexane containing a small amount of methanol and the resulting solid was collected washed and dried to give 5-{[4-(2,3-dichlorophenyl)-3-ethoxycarbonyl-5-methoxycarbonyl-6-methyl-1,4-dihydropyridin-2-yl]methoxymethyl}-2-[2-(3-cyano-2-methyl-1-isothioureido)ethyl]tetrazole (0.75 g), m.p. 78°–80° C. Found: C,48.53; H,4.93; N,17.60. $C_{25}H_{28}Cl_2N_8O_5S$ requires C,48.23; H,4.34; N,18.00%.

(B) A solution of the product from (A) above (0.72 g) and hydrazine hydrate (0.20 g) in ethanol (15 ml) was heated under reflux for 2 hours and then evaporated. The residue was twice taken up in toluene and evaporated. The residual oil was triturated with diethyl ether/hexane and the resulting solid collected, recrystallised twice from toluene and dried to give the title compound (139 mg), m.p. 85° C. Found: C,47.99; H,4.92; N,22.50. $C_{24}H_{28}Cl_2N_{10}O_5$ requires: C,47.44; H,4.61; N,23.06%.

EXAMPLE 28

1-{2-[(3-Amino-1,2,4-triazol-5-yl)amino]ethyl}-5-{[4-(2,3-dichlorophenyl)-3-ethoxycarbonyl-5-methoxycarbonyl-6-methyl-1,4-dihydropyridin-2-yl]methoxymethyl}tetrazole This compound was prepared by the procedure described above in Example 27 but starting with 1-(2-aminoethyl)-5-{[4-(2,3-dichlorophenyl)-3-ethoxycarbonyl-5-methoxycarbonyl-6-methyl-1,4-dihydropyridin-2-yl]methoxymethyl}tetrazole. The product was characterised as a hemihydrate, m.p. 70° C. Found: C,46.86; H,5.15; N,22.12. $C_{24}H_{27}Cl_2N_{10}O_5.0.5H_2O$ requires C,46.75; H,4.71; N,22.72%.

EXAMPLE 29

5-{[4-(2,3-Dichlorophenyl)-3-ethoxycarbonyl-5-methoxycarbonyl-6-methyl-1,4-dihydropyridin-2-yl]methoxymethyl}-2-{2-[6-(4-morpholinyl)-4-pyrimidinylamino]ethyl}tetrazole A solution of 2-(2-aminoethyl)-5-{[4-(2,3-dichlorophenyl)-3-ethoxycarbonyl-5-methoxycarbonyl-6-methyl-1,4-dihydropyridin-2-yl]methoxymethyl}tetrazole (0.52 g), triethylamine (0.5 ml) and 4,6-dichloropyrimidine (0.16 g) in ethanol (20 ml) was heated under reflux for 23 hours and then evaporated. The residue was purified by chromatography on silica (8 g) using dichloromethane plus from 0 to 100% by volume of ethyl acetate as eluant. Appropriate fractions were combined and evaporated to give 2-{[(6-chloro-4-pyrimidinyl)amino]ethyl}-5-{[4-(2,3-dichlorophenyl)-3-ethoxycarbonyl-5-methoxycarbonyl-6-methyl-1,4-dihydropyridin-2-yl]methoxymethyl}tetrazole (0.51 g) as a colourless foam. A solution of this crude product in morpholine (3 ml) was heated on a steam-bath for 90 minutes and then partitioned between 2M hydrochloric acid and dichloromethane. The acidic layer was extracted into dichloromethane and the combined organic layers were washed with water and 10% aqueous sodium carbonate solution, dried over anhydrous sodium sulphate and evaporated. The residue was purified by chromatography on silica (10 g) using dichloromethane plus from 0 to 50% by volume of ethyl acetate followed by dichloromethane plus from 1 to 5% by volume of methanol as eluant. Appropriate fractions were combined and evaporated. The residual oil was triturated with diethyl ether and the resulting solid collected, washed with diethyl ether and dried to give the title compound (0.51 g), m.p. 160°–162° C. Found: C,52.24; H,5.20; N,18.24. $C_{30}H_{35}Cl_2N_9O_6$ requires: C,52.33; H,5.09; N,18.31%.

EXAMPLE 30

5-{[4-(2,3-Dichlorophenyl)-3-ethoxycarbonyl-5-methoxycarbonyl-6-methyl-1,4-dihydropyridin-2-yl]methoxymethyl}-1-{2-[6-(4-morpholinyl)-4-pyrimidinylamino]ethyl}tetrazole This compound was prepared by the method described above in Example 29 but starting with 1-(2-aminoethyl)-5-{[4-(2,3-dichlorophenyl)-3-ethoxycarbonyl-5-methoxycarbonyl-6-methyl-1,4-dihydropyridin-2-yl]methoxymethyl}tetrazole. The product was characterised as a dihydrate, m.p. 179°–181° C. dec. Found: C,49.56; H,5.29; N,17.11. $C_{30}H_{35}Cl_2N_9O_6.2H_2O$ requires: C,49.70; H,5.39; N,17.40%.

EXAMPLE 31

5-{[4-(2,3-Dichlorophenyl)-3-ethoxycarbonyl-5-methoxycarbonyl-6-methyl-1,4-dihydropyridin-2-yl]methoxymethyl}-2-{2-[(4,5-dihydro-4-oxo-(4H)-thiazol-2-yl)amino]ethyl}tetrazole Thiophosgene (138 mg) was added to a rapidly stirred mixture of 2-(2-aminoethyl)-5-{[4-(2,3-dichlorophenyl)-3-ethoxycarbonyl-5-methoxycarbonyl-6-methyl-1,4-dihydropyridin-2-yl]methoxymethyl}tetrazole (0.52 g) and calcium carbonate (390 mg) in a mixture of water (10 ml) and dichloromethane (20 ml). The mixture was stirred at room temperature for 16 hours filtered and the filtrate washed with 2M hydrochloric acid and water, dried over anhydrous sodium sulphate and evaporated. The residue was dissolved in saturated ethanolic ammonia (10 ml) and the solution heated under reflux for 3 hours and then evaporated. The residue was dissolved in dichloromethane (10 ml) and the solution treated with triethylamine (0.5 ml) and ethyl bromoacetate (0.20 g), stirred at room temperature for 16 hours, filtered and evaporated. The residue was purified by chromatography on silica (10 g) using dichloromethane plus from 0 to 5% by volume of methanol as eluant. Appropriate fractions were combined and evaporated. The residual oil was triturated with hexane and the resulting solid collected, recrystallised from ethyl acetate and dried to give the title compound (54 mg), m.p. 80°–82° C. Found: C,47.90; H,4.32; N,15.02. $C_{25}H_{27}Cl_2N_7O_6S$ requires: C,48.07; H,4.33; N,15.71%.

EXAMPLE 32

5-{[4-(2,3-Dichlorophenyl)-3-ethoxycarbonyl-5-methoxycarbonyl-6-methyl-1,4-dihydropyridin-2-yl]methoxymethyl}-2-(2-mesylaminoethyl)tetrazole A solution of 2-(2-aminoethyl)-5-{[4-(2,3-dichlorophenyl)-3-ethoxycarbonyl-5-methoxycarbonyl-6-methyl-1,4-dihydropyridin-2-yl]methoxymethyl}tetrazole (0.33 g), triethylamine (65 mg) and methanesulphonyl chloride (71 mg) in dichloromethane (15 ml) was heated under reflux for 2 hours and then evaporated. The residue was purified by chromatography on silica (6 g) using dichloromethane plus from 0 to 1% by volume of methanol as eluant. Appropriate fractions were combined and evaporated. The residual solid was recrystallized from ethyl acetate and dried to give the title compound (111 mg) as a hydrate, m.p. 245°–247° C. Found:

C,46.23; H,5.02; N,13.82. $C_{23}H_{28}Cl_2N_6O_7S.H_2O$ requires: C,46.26; H,5.19; N,14.08%.

EXAMPLE 33

5-{[4-(2,3-Dichlorophenyl)-3-ethoxycarbonyl-5-methoxycarbonyl-6-methyl-1,4-dihydropyridin-2-yl]methoxymethyl}-2-[2-(quinoline-8-sulphonylamino)ethyl]tetrazole was prepared by the method described above in Example 32 but using quinoline-8-sulphonyl chloride instead of methanesulphonyl chloride. The product had m.p. 98°-100° C. Found: C,52.28; H,4.73; N,13.41. $C_{31}H_{31}Cl_2N_7O_7S$ requires: C,51.95; H,4.33; N,13.69%.

EXAMPLE 34

5-{[4-(2,3-Dichlorophenyl)-3-ethoxycarbonyl-5-methoxycarbonyl-6-methyl-1,4-dihydropyridin-2-yl]methoxymethyl}-2-{2-[5-(4-morpholinylsulphonyl)-2-pyridinylamino]ethyl}tetrazole A solution of 2-(2-aminoethyl)-5-{[4-(2,3-dichlorophenyl)-3-ethoxycarbonyl-5-methoxycarbonyl-6-methyl-1,4-dihydropyridin-2-yl]methoxymethyl}tetrazole (0.33 g), 2-chloro-5-(4-morpholinylsulphonyl)pyridine (145 mg) and triethylamine (65 mg) in dichloromethane (15 ml) was heated under reflux for 2 hours, then stirred at room temperature for 16 hours and evaporated. The residue was purified by chromatography on silica (6 g) using dichloromethane plus from 0 to 5% by volume of methanol as eluant. Appropriate fractions were combined and evaporated to give the title compound (84 mg), m.p. 112°-114° C. Found: C,56.32; H,5.90; N,10.45. $C_{31}H_{36}Cl_2N_8O_8S$ requires: C,56.13; H,5.80; N,10.48%.

EXAMPLE 35

2-{[4-(2,3-Dichlorophenyl)-3-ethoxycarbonyl-5-methoxycarbonyl-6-methyl-1,4-dihydropyridin-2-yl]methoxymethyl}-5-dimethylaminomethyl-1,3,4-thiadiazole A mixture of 1-<2-{[4-(2,3-dichlorophenyl)-3-ethoxycarbonyl-5-methoxycarbonyl-6-methyl-1,4-dihydropyridin-2-yl]methoxy}-acetyl>-2-(2-dimethylaminoacetyl)hydrazine (0.26 g) and Lawesson's reagent (0.22 g) in acetonitrile (10 ml) was stirred at room temperature for 48 hours and then evaporated. The residue was purified by chromatography on silica (8 g) using dichloromethane plus from 0 to 10% by volume of methanol as eluant. Appropriate fractions were combined and evaporated and the residue recrystallised from methanol to give the title compound as a hemihydrate (49 mg), m.p. 168°-170° C. Found: C,54.36; H,5.61; N,10.59. $C_{24}H_{29}ClN_4O_5S.0.5H_2O$ requires: C,54.39; H,5.66; N,10.57%.

EXAMPLES 36-39

The following compounds were prepared by the method described above in Example 35 by reacting the appropriate diacylhydrazine with Lawesson's reagent and were characterised in the form indicated:

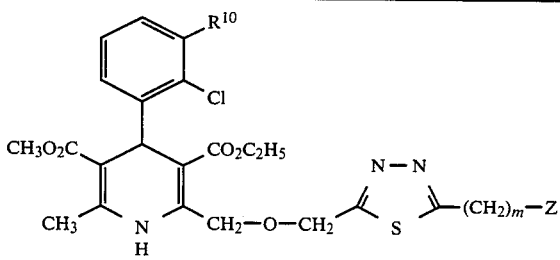

| Example No. | $R^{10}$ | —(CH$_2$)$_m$—Z | Form Characterised | m.p. (°C.) | C | H | N |
|---|---|---|---|---|---|---|---|
| 36 | H | —CH$_2$N(morpholino) | Free base | 134–136 | 55.41 (55.47 | 5.60 5.51 | 10.00 9.96) |
| 37 | H | —CH$_2$CH$_2$N(CH$_3$)$_2$ | Free base | 115–116 | 56.32 (56.13 | 5.90 5.80 | 10.45 10.48) |
| 38 | Cl | —CH$_2$N(morpholino) | Free base | 175–176 | 52.08 (52.08 | 5.22 5.34 | 9.05 9.35) |
| 39 | Cl | —CH$_2$CH$_2$N(CH$_3$)$_2$ | Hemihydrate | 160–161 | 51.66 (51.72 | 5.26 5.68 | 9.81 9.65) |
| 40 | Cl | —CH$_2$CH$_2$N(phthalimido) | Hemihydrate | 92–93 | 54.61 (54.71 | 4.69 4.26 | 8.06 8.23) |

EXAMPLE 41

4-(2-Aminoethyl)-2-{[4-(2-chlorophenyl)-3-ethoxycarbonyl-5-methoxycarbonyl-6-methyl-1,4-dihydropyridin-2-yl]methoxymethyl}thiazole (A) A mixture of 2-{[4-(2-chlorophenyl)-3-ethoxycarbonyl-5-methoxycarbonyl-6-methyl-1,4-dihydropyridin-2-yl]methoxy}thioacetamide (2.19 g) and 1-bromo-4-phthalimido-2-butanone (1.48 g) in ethanol (50 ml) was heated under reflux for 4 hours and then evaporated. The residue was triturated with ether/hexane and the resulting solid collected, recrystallised from methanol and dried to give 2-{[4-(2-chlorophenyl)-3-ethoxycarbonyl-5-methoxycarbonyl-6-methyl-1,4-dihydropyridin-2-yl]methoxymethyl}-4-(2-phthalimidoethyl)thiazole as a hemihydrate (1.73 g), m.p. 156°–157° C. Found: C,59.71; H,5.06; N,6.31. $C_{32}H_{29}ClN_3O_7S.0.5-H_2O$: requires C,59.58; H,4.80; N,6.51%.

(B) A solution of the product from (A) above (1.60 g) in 25% aqueous methylamine (60 ml) was stirred at room temperature for 16 hours and then evaporated. The residue was partitioned between ethyl acetate and 10% aqueous sodium carbonate solution and the organic layer was washed with saturated brine, dried over anhydrous sodium sulphate and evaporated. The residue was dissolved in diethyl ether and the solution treated with excess ethereal hydrogen chloride solution. The precipitated oil was triturated with diethyl ether and the resulting solid collected, washed with diethyl ether and dried to give the title compound as a dihydrochloride monohydrate (0.92 g), m.p. 168°–170° C. Found: C,48.38; H,5.95; N,7.00. $C_{24}H_{28}ClN_3O_5S.2HCl.H_2O$ requires: C,48.28; H,5.36; N,7.04%.

EXAMPLE 42

4-(2-Aminoethyl)-2-{[4-(2,3-dichlorophenyl)-3-ethoxycarbonyl-5-methoxycarbonyl-6-methyl-1,4-dihydropyridin-2-yl]methoxymethyl}thiazole This compound was prepared by the method described in Example 41 but using 2-{[4-(2,3-dichlorophenyl)-3-ethoxycarbonyl-5-methoxycarbonyl-6-methyl-1,4-dihydropyridin-2-yl]methoxy}thioacetamide as starting material. The product was characterised as a hydrochloride monohydrate, m.p. 110°–112° C. Found: C,48.44; H,4.99; N,7.15. $C_{24}H_{27}Cl_2N_3O_5S.HCl.H_2O$ requires: C,48.44; H,5.04; N,7.06%.

EXAMPLE 43

5-(2-Aminoethyl)-B 2-{[4-(2,3-dichlorophenyl)-3-ethoxycarbonyl-5-methoxycarbonyl-6-methyl-1,4-dihydropyridin-2-yl]methoxymethyl}1,3,4-thiadiazole This compound was prepared by the method described in Example 41(B) but starting with 2-{[4-(2,3-dichlorophenyl)-3-ethoxycarbonyl-5-methoxycarbonyl-6-methyl-1,4-dihydropyridin-2-yl]methoxymethyl}-5-(2-phthalimidoethyl)-1,3,4-thiadiazole. The product had m.p. 138°–140° C. Found: C,50.89; H,4.95; N,10.22. $C_{23}H_{26}Cl_2N_4O_5S$ requires: C,51.02; H,4.80; N,10.35%.

EXAMPLE 44

2-{[4-(2-Chlorophenyl)-3-ethoxycarbonyl-5-methoxycarbonyl-6-methyl-1,4-dihydropyridin-2-yl]methoxymethyl}-5-[(4-methylpiperazinyl)methyl]furan oxalate A solution of ethyl 4-<{5-[(4-methyl-piperazinyl)methyl]-2-furyl}methoxy>acetoacetate (6.76 g), 2-chlorobenzaldehyde (2.81 g), methyl 3-aminocrotonate (2.30 g) and acetic acid (2 ml) in ethanol (15 ml) was heated under reflux for 4 hours. The solution was evaporated and the residue partitioned between 2M hydrochloric acid and toluene. The acidic layer was basified with sodium carbonate and extracted into diethyl ether. The ether extract was dried over anhydrous magnesium sulphate and evaporated and the residue purified by chromatography on silica (10 g) using petroleum ether (b.p. 40°–60° C.) plus from 50 to 100% by volume of dichloromethane as eluant. Appropriate fractions were combined and evaporated. The residue was dissolved in diethyl ether and the solution treated with a solution of excess oxalic acid in diethyl ether. The resulting precipitate was collected and recrystallised from methanol to give the title compound, m.p. 199°–200° C. (with decomposition). Found: C,53.69; H,5.46; N,5.69. $C_{29}H_{36}ClN_3O_6.(CO_2H)_2$ requires: C,53.60; H,5.28; N,5.43%.

EXAMPLE 45

2-{[4-(2-Chlorophenyl)-3-ethoxycarbonyl-5-methoxycarbonyl-6-methyl-1,4-dihydropyridin-2-yl]methoxymethyl}-5-dimethylaminomethylthiophene This compound was prepared as described in Example 44 above but using ethyl 4-(5-dimethylaminomethyl-2-thienyl)methoxyacetoacetate instead of ethyl 4-<{5-[(4-methylpiperazin-1-yl)methyl]-2-furyl}methoxy>acetoacetate as the starting material. The product was characterised as the free base, m.p. 81°–83° C. Found: C,59.79; H,6.01; N,5.32. $C_{26}H_{31}ClNO_5S$ requires: C,60.16; H,6.02; N,5.40%.

EXAMPLE 46

2-{[4-(2-Chlorophenyl)-3-ethoxycarbonyl-5-methoxycarbonyl-6-methyl-1,4-dihydropyridin-2-yl]methoxymethyl}-5-(4-morpholinylmethyl)furan This compound was prepared as described in Example 45 above but using ethyl 4-[5-(4-morpholinylmethyl)-2-furyl]methoxy-acetoacetate as the starting material. The product was characterised as the free base, m.p. 85°–87° C. Found: C,61.33; H,6.15; N,5.16. $C_{28}H_{33}ClN_2O_7$ requires: C,61.70; H,6.10; N,5.14%.

PREPARATION 1

1-<2-{[4-(2-Chlorophenyl)-3-ethoxycarbonyl-5-methoxycarbonyl-6-methyl-1,4-dihydropyridin-2-yl]methoxy}acetyl>-2-[2-(4-morpholinyl)acetyl]hydrazine A solution of 2-{[4-(2-chlorophenyl)-3-ethoxycarbonyl-5-methoxycarbonyl-6-methyl-1,4-dihydropyridin-2-yl]methoxy}acetic acid (1.69 g), 1-(3-dimethylaminopropyl)-3-ethylcarbodiimide hydrochloride (1.62 g) and triethylamine (0.5 ml) in tetrahydrofuran (30 ml) was stirred at room temperature for 1 hour and then treated with 2-(4-morpholinyl)acetylhydrazine (0.63 g). The mixture was stirred at room temperature for 16 hours and evaporated. The residue was partitioned between water and ethyl acetate and the organic layer dried over anhydrous sodium sulphate and evaporated. The residue was triturated with hexane and the resulting solid collected, recrystallised from toluene and dried to give the title compound (1.18 g), m.p. 100°–105° C. Found: C,55.33; H,6.20; N,9.72. $C_{26}H_{33}ClN_4O_8$ requires: C,55.27; H,5.85; N,9.92%.

PREPARATIONS 2-5

The following compounds were prepared by the method described in Preparation 1 from the appropriate starting materials.

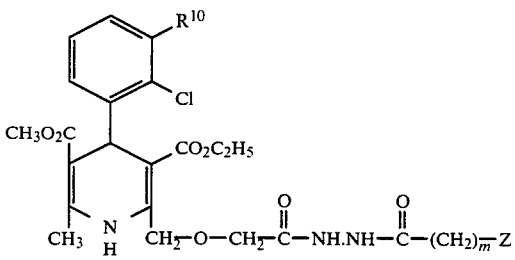

| Preparation No. | R[10] | —(CH₂)ₘ—Z | m.p. (°C.) | Analysis % (Theoretical in Brackets) | | |
|---|---|---|---|---|---|---|
| | | | | C | H | N |
| 2 | H | —CH₂N(CH₃)₂ | 177–178 | 55.07 (55.12 | 6.03 5.93 | 10.83 10.72) |
| 3 | H | —CH₂CH₂N(CH₃)₂ | 115–117 | Characterised by spectral data | | |
| 4 | Cl | —CH₂N⟨O⟩ | 105–106 | 52.68 (52.09 | 5.61 5.34 | 8.77 9.35) |
| 5 | Cl | —CH₂CH₂N(CH₃)₂ | 173–175 | 52.58 (52.54 | 5.66 5.60 | 10.02 9.81) |

PREPARATION 6

1-<2-{[4-(2-Chlorophenyl)-3-ethoxycarbonyl-5-methoxycarbonyl-6-methyl-1,4-dihydropyridin-2-yl]methoxy}acetyl>-2-(3-phthalimidopropionyl)hydrazine A mixture of 2-{[4-(2-chlorophenyl)-3-ethoxycarbonyl-5-methoxycarbonyl-6-methyl-1,4-dihydropyridin-2-yl]methoxy}acetylhydrazine (4.70 g), 3-phthalimidopropionyl chloride (2.40 g) and potassium carbonate (1.38 g) in dichloromethane (80 ml) was heated under reflux for 24 hours and then evaporated. The residue was partitioned between ethyl acetate and 10% aqueous sodium carbonate solution and the organic layer dried over anhydrous sodium sulphate and evaporated. The residue was purified by chromatography on silica (30 g) eluting with hexane plus from 70 to 100% by volume of dichloromethane followed by dichloromethane plus from 0 to 2% by volume of methanol. Appropriate fractions were combined and evaporated. The residue was triturated with diethyl ether/hexane and the resulting solid collected, washed with diethyl ether and dried to give the title compound (2.70 g), which was used directly in Example 40.

PREPARATION 7

Ethyl 4-<{5-[(4-methyl-1-piperazinyl)methyl]-2-furyl}methoxy>acetoacetate (4-Methyl-1-piperazinyl)furan-2-methanol (10.0 g) was added dropwise to a stirred suspension of sodium hydride (4.4 g; 50% dispersion in oil) in tetrahydrofuran (80 ml). The mixture was warmed on a steam-bath for 5 minutes, cooled to room temperature and treated with a solution of ethyl 4-chloroacetoacetate (7.8 g) in tetrahydrofuran (20 ml) dropwise over 2 hours. The mixture was stirred at room temperature for 16 hours, quenched with ethanol and poured onto ice (100 g). The pH was adjusted to 6 with concentrated hydrochloric acid and the mixture extracted three times with ethyl acetate. The combined ethyl acetate extracts were dried over anhydrous magnesium sulphate and evaporated. The residue was partitioned between acetonitrile and petroleum ether (b.p. 40°-60° C.) and the acetonitrile layer evaporated to give the title compound as a brown oil. This product was shown to be essentially pure by n.m.r. spectroscopy and was used directly in the subsequent reaction.

PREPARATION 8

Ethyl 4-(5-dimethylaminomethyl-2-thienyl)methoxyacetoacetate was prepared as described above in Preparation 7 starting with 5-dimethylaminomethylthiophene-2-methanol.

PREPARATION 9

Ethyl 4-[5-(4-morpholinylmethyl)-2-furyl]methoxyacetoacetate was prepared as described above in Preparation 7 starting with 5-(4-morpholinyl)furan-2-methanol.

PREPARATION 10

2-{[4-(2-Chlorophenyl)-3-ethoxycarbonyl-5-methoxycarbonyl-6-methyl-1,4-dihydropyridin-2-yl]methoxy}acetamide Carbonyldiimidazole (9.80 g) was added to a suspension of 2-{[4-(2-chlorophenyl)-3-ethoxycarbonyl-5-methoxycarbonyl-6-methyl-1,4-dihydropyridin-2-yl]methoxy}acetic acid (25.4 g) in tetrahydrofuran (400 ml) and the mixture stirred at room temperature for 2 hours. A stream of gaseous ammonia was passed through the resulting solution with stirring until the reaction was complete (as determined by t.l.c.). The reaction mixture was evaporated and the residue partitioned between ethyl acetate and water. The organic layer was washed with water, dried over sodium sulphate and evaporated. The residue was triturated with diethyl ether and the resulting solid collected, recrystalised from diethyl ether/n-hexane and dried to give the title compound (17.0 g), m.p. 127°–128° C. Found: C,56.70; H,5.42; N,6.60. $C_{20}H_{23}ClN_2O_6$ requires: C,56.60; H,5.48; N,6.63%.

PREPARATION 11

2-{[4-(2-Chlorophenyl)-3-ethoxycarbonyl-5-methoxycarbonyl-6-methyl-1,4-dihydropyridin-2-yl]methoxy}thioacetamide A mixture of 2-{[4-(2-chlorophenyl)-3-ethoxycarbonyl-5-methoxycarbonyl-6-methyl-1,4-dihydropyridin-2-yl]methoxy}acetamide (6.8 g) and Lawesson's reagent (6.4 g) in acetonitrile (300 ml) was stirred at room temperature for 2.5 hours, filtered and evaporated. The residue was purified by chromatography on silica (80 g) using dichloromethane plus 0–10% v/v ethyl acetate as eluant. Appropriate fractions were combined and evaporated and the residual oil triturated with diethyl ether. The resulting solid was collected, washed with diethyl ether and dried to give the title compound (5.9 g), m.p. 149°–150° C. Found: C,54.38; H,5.29; N,6.37. $C_{20}H_{23}ClN_2O_5S$ requires: C,54.74; H,5.28; N,6.38%.

We claim:

1. A compound having the formula:

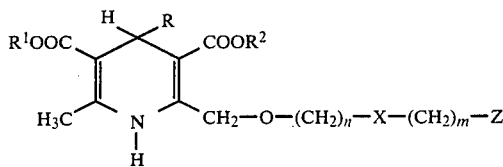

(I)

or a pharmaceutically acceptable salt thereof;
wherein
    R is aryl or heteroaryl;
    $R^1$ and $R^2$ are each independently $C_1$-$C_4$ alkyl or 2-methoxyethyl;
    n is 1 or 2;
    m is 1, 2 or 3;
    X is a 5 or 6 membered aromatic heterocyclic group which is linked to the adjacent alkoxymethyl group by a ring carbon atom thereof; and
    Z is a group —$NR^3R^4$ or a 5 or 6 membered nitrogen containing heterocyclic group;
wherein
    $R^3$ is H or $C_1$-$C_4$ alkyl;
    $R^4$ is H, $C_1$-$C_4$ alkyl, $CO(C_1$-$C_4$ alkyl), $COCF_3$, $CONR^5R^6$, $SO_2(C_1$-$C_4$ alkyl) or a heterocyclic or $SO_2$-heterocyclic group, wherein the heterocyclic group is optionally substituted; and
    $R^5$ and $R^6$ are each independently H or $C_1$-$C_4$ alkyl or taken together with the nitrogen atom to which they are attached, they form a pyrrolidinyl, piperidyl, morpholino, piperazinyl or $N$-($C_1$-$C_4$ alkyl)-piperazinyl group.

2. A compound according to claim 1, wherein R is "aryl" and "aryl" is phenyl; phenyl substituted by one or two substituents each independently selected from the group consisting of nitro, halo, $C_1$-$C_4$ alkyl, $C_1$-$C_4$ alkoxy, hydroxy, trifluoromethyl and cyano; or is 1- or 2-naphthyl; or wherein R is "heteroaryl" and "heteroaryl" is benzofuranyl; benzothienyl; pyridyl; pyridyl substituted by methyl, methylthio, cyano or halo; quinolyl; benzoxazolyl; benzthiazolyl; furyl; pyrimidinyl thiazolyl; 2,1,3-benzoxadiazol-4-yl; 2,1,3-benzothiadiazol-4-yl; thienyl; or thienyl monosubstituted by halo or $C_1$-$C_4$ alkyl.

3. A compound according to clam 2 wherein R is 2-chlorophenyl or 2,3-dichlorophenyl.

4. A compound according to claim 3 wherein $R^1$ is $CH_3$, $R^2$ is $C_2H_5$, n is 1 and m is 2.

5. A compound according to claim 4 wherein X is tetrazolyl, thiadiazolyl, thiazolyl, thienyl or furyl.

6. A compound according to claim 5 wherein Z is a pyridyl, pyrimidinyl, triazinyl, pyrrolyl, imidazolyl, triazolyl, tetrazolyl, thiazolyl, thiadiazolyl, oxadiazolyl, pyrrolidinyl, piperidyl, morpholino or piperazinyl group and said group is unsubstituted or substituted with $C_1$-$C_4$ alkyl, trifluoroacetyl, arylamino, carbamoyl, methylcarbamoyl, amino or di($C_1$-$C_4$ alkyl)amino groups.

7. A compound according to claim 6 wherein Z is 2-pyridyl, 4-imidazolyl, morpholino, 1,4-piperazinyl, 4-trifluoroacetyl-1-piperazinyl or 4-methylcarbamoyl-1-piperazinyl.

8. A compound according to claim 5 wherein Z is $NH_2$, $NHCH_3$ or $NH(CH_3)_2$.

9. A compound according to claim 1 wherein R is 2,3-dichlorophenyl, $R^1$ is methyl, $R^2$ is ethyl, n is 1, X is 1-thia-3,4-diazolyl, m is 1 and Z is morpholino.

10. A pharmaceutical composition comprising a compound according to claim 1 and a pharmaceutically acceptable diluent or carrier.

11. A method of treating or preventing hypertension in man which comprises administering an antihypertensive effect amount of a compound according to claim 1.

12. A method for treating or preventing ischaemic heart condition in man which comprises administering an anti-ischaemic effective amount of a compound according to claim 1.

* * * * *